(12) United States Patent
Koenig et al.

(10) Patent No.: US 10,104,894 B2
(45) Date of Patent: Oct. 23, 2018

(54) SELF-REGENERATING ANTIMICROBIAL COMPOSITION AND METHOD OF USE

(71) Applicant: Kimberly-Clark Worldwide, Inc., Neenah, WI (US)

(72) Inventors: David W. Koenig, Neenah, WI (US); Douglas R. Hoffman, Greenville, WI (US); Cindy Korir-Morrison, Smyrna, GA (US); Amy L. Vanden Heuvel, Hortonville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 15/129,668

(22) PCT Filed: Mar. 18, 2015

(86) PCT No.: PCT/US2015/021181
§ 371 (c)(1),
(2) Date: Sep. 27, 2016

(87) PCT Pub. No.: WO2015/153119
PCT Pub. Date: Oct. 8, 2015

(65) Prior Publication Data
US 2017/0172153 A1    Jun. 22, 2017

Related U.S. Application Data

(60) Provisional application No. 61/972,816, filed on Mar. 31, 2014.

(51) Int. Cl.
| | | |
|---|---|---|
| *A01N 63/00* | (2006.01) | |
| *A01N 25/10* | (2006.01) | |
| *C09D 5/14* | (2006.01) | |
| *A01N 25/34* | (2006.01) | |
| *C12N 7/00* | (2006.01) | |

(52) U.S. Cl.
CPC .............. *A01N 63/00* (2013.01); *A01N 25/10* (2013.01); *A01N 25/34* (2013.01); *C09D 5/14* (2013.01); *C12N 7/00* (2013.01); *C12N 2750/00031* (2013.01)

(58) Field of Classification Search
CPC ......... A01N 63/00; A01N 25/10; A01N 25/34
See application file for complete search history.

(56) References Cited

U.S. PATENT DOCUMENTS

| 5,451,353 A * | 9/1995 | Rezai ................ A61F 13/53 264/109 |
| 5,658,779 A | 8/1997 | Krupey et al. |
| 5,846,604 A | 12/1998 | Caldwell |
| 6,469,177 B1 | 10/2002 | Worley et al. |
| 6,703,040 B2 | 3/2004 | Katsarava et al. |
| 6,737,079 B2 | 5/2004 | Fischetti et al. |
| 6,969,769 B2 | 11/2005 | Worley et al. |
| 7,332,307 B2 | 2/2008 | Carlton et al. |
| 7,482,115 B2 | 1/2009 | Scott et al. |
| 7,541,398 B2 | 6/2009 | Sun et al. |
| 8,309,077 B2 | 11/2012 | Murthy et al. |
| 2002/0001590 A1 | 1/2002 | Kelly et al. |
| 2009/0081173 A1 | 3/2009 | Serwer |
| 2009/0191254 A1 | 7/2009 | Curtin et al. |
| 2009/0297587 A1 * | 12/2009 | Yang ................ A61L 15/44 424/445 |
| 2010/0291041 A1 | 11/2010 | Dahlen et al. |
| 2012/0213759 A1 | 8/2012 | Karsten et al. |
| 2013/0025764 A1 | 1/2013 | Henderson |
| 2013/0156697 A1 | 6/2013 | Vitaliano et al. |
| 2014/0080977 A1 | 3/2014 | Youngblood et al. |

FOREIGN PATENT DOCUMENTS

| EP | 0 414 304 B1 | 11/1994 |
| WO | WO 2013/007289 A1 | 1/2013 |
| WO | WO 2013/048604 A2 | 4/2013 |
| WO | WO 2013/098547 A1 | 7/2013 |

OTHER PUBLICATIONS

The Dow Chemical Company, Product Safety Assessment SoftCAT(TM) Polymers, http://msdssearch.dow.com/PublishedLiteratureDOWCOM/dh_019b/0901b8038019bb8a.pdf?filepath=productsafety/pdfs/noreg/233-00447.pdf&fromPage=GetDoc, 2008.*
Troller, John A. and Christian, J.H.B., Water Activity and Food, 1978, Chapter 1, pp. 1-3., New York, New York.

* cited by examiner

*Primary Examiner* — Rosanne Kosson
(74) *Attorney, Agent, or Firm* — Kimberly-Clark Worldwide, Inc.

(57) ABSTRACT

A composition may be applied to animate and inanimate surfaces to render such surfaces antimicrobial for as long as the composition remains on the surface. The composition contains at least one pathogen-associated virus that is self-regenerating so that a user need not take steps to regenerate the material. The virus is or viruses are contained within a polymer matrix. The polymer matrix has the ability to maintain a desired moisture content to support the regeneration of the virus(es). Various methods of using the composition include the coating of animate and inanimate surfaces to prevent bacterial, viral, and fungal infections.

13 Claims, No Drawings

SELF-REGENERATING ANTIMICROBIAL COMPOSITION AND METHOD OF USE

CROSS-REFERENCE TO RELATED APPLICATIONS

This application claims the benefit of U.S. Provisional Application No. 61/972,816 entitled "Self-Regenerating Antimicrobial Composition and Method of Use" and filed in the U.S. Patent and Trademark Office on Mar. 31, 2014. The entirety of the prior application is hereby incorporated by reference in this application.

BACKGROUND

The disclosure relates to antimicrobial compositions that contain pathogen-specific viruses, and their use in killing pathogenic organisms or inhibiting the growth thereof.

Antimicrobial compositions for skin, fabrics or hard surfaces are commonly used to prevent the spread of infectious bacteria and/or microbial contamination. There are many antimicrobial compositions on the market today, but most of them become spent or are consumed, leaving a protected surface suddenly unprotected from microbes.

Some antimicrobial compositions can be regenerated so that they can continue to kill microbes. In one example, cellulose materials were treated with an antimicrobial coating containing hydantoin derivatives. This biocidal compound can be regenerated after it is comes in contact with chlorine bleach. The drawback to this composition is that it does have a finite life span in which it demonstrates biocidal activity against pathogenic microorganisms, and it relies on the user to regenerate the composition's ability to kill microbes.

What is desired is an antimicrobial composition that can be regenerated without user input. Further desired is a composition that maintains its antimicrobial activity for as long as it remains on the surface.

SUMMARY

A composition for protecting a surface from microbial contamination is disclosed. The composition includes a polymer matrix with a virus contained therein. The polymer matrix is configured to retain water so that the virus can self-regenerate upon exposure to a microbe.

These and other aspects, features and advantages of the present disclosure should be apparent to those skilled in the art from the following detailed description.

DETAILED DESCRIPTION OF THE DISCLOSURE

In one embodiment, the present disclosure is a composition that can coat animate and inanimate surfaces, and render such surfaces antimicrobial for as long as it remains on the surface. The composition contains at least one pathogen-associated virus that is self-regenerating so that a user need not take steps to regenerate the material. The virus or viruses which are contained within a polymer matrix, perform the antimicrobial function and are pathogen specific. The polymer matrix has the ability to maintain a desired moisture content to support the regeneration of the virus(es). Also disclosed are methods of using the composition.

Examples of inanimate surfaces that can be coated with the composition of the present disclosure include, but are not limited to cellulose, chitin, chitosan, synthetic fibers, glass, ceramics, porcelain, plastics, rubber, cement grout, latex, caulk, acrylic, vinyl, polyurethanes, silicon tubing, marble or other stone, metals, metal oxides, silica, and plants. Examples of animate surfaces that can be coated with the composition of the present disclosure include hair, nails, bone, and skin.

The composition of the present disclosure may be designed to inactivate pathogenic organisms such as bacteria, fungi (yeast, mold), protozoans, annelids, and arthopods. It can be used to prevent the spread of infectious diseases including MRSA, control noxious odors, control discoloration due to mildew, and the like. In one aspect, such a composition may be used to coat machinery, process lines, water distribution lines, metal-working fluid systems, and the like to inhibit biofilm and corrosion. In another aspect, such a composition may be used in the medical field to coat tubing used in the body (catheters, feeding tubes, tracheotomy tubes and the like), surgical equipment, doorknobs, handles, beds, computers and other equipment. In yet another aspect, such a composition may be used in the agricultural field to coat plants to prevent bacterial and fungal infections, and insects. Milk producers, meat processors and food manufacturers would also benefit from coating inanimate surfaces coming into contact with food. Of course, the composition may be used to coat inanimate surfaces in the home and in institutional settings. The possibilities to coat inanimate surfaces are too many to describe in this disclosure. Finally, animate surfaces such as skin, mucosa, hair and nails may be coated with the composition to prevent bacterial and/or fungal infection.

Polymer Matrix

A polymer matrix is used to contain the pathogen-specific virus. The polymer matrix has the following characteristics: 1) it can absorb water, 2) it can maintain a Water of Activity of greater than 0.65 for about 5 to about 40 minutes after it is challenged with the pathogen to be killed, or in the alternative about 10 to about 30 minutes, or in the alternative, about 15 to about 25 minutes, 3) it can cover and adhere to surfaces having different textures and shapes, 4) it may be transparent and colorless, but may be colored and made opaque with additives, 5) it can be flexible if desired, 6) it can be applied as a powder, spray or foam; or rolled, dipped, wiped or brushed onto a surface. Other characteristics are possible.

In one embodiment, the polymer matrix is a hydrogel. A hydrogel is a network of polymer chains that are hydrophilic, sometimes found as a colloidal gel in which water is the dispersion medium. Hydrogels are highly absorbent natural or synthetic polymers that can contain over 99.9% water. Hydrogels also possess a degree of flexibility due to their significant water content. Common ingredients include polyvinyl alcohol, sodium polyacrylate, acrylate polymers and copolymers with an abundance of hydrophilic groups. Natural hydrogel materials include agarose, methylcellulose, hyaluronan, and other naturally derived polymers.

In one embodiment the polymer matrix is the superabsorbent polymer solution in U.S. Pat. No. 6,849,685 to Soerens et al., U.S. Pat. No. 7,312,286 to Lang et al., and U.S. Pat. No. 7,335,713 to Lang et al., the entirety of each of these references is herein incorporated by reference. Such polymer solution may be referred to as flexible absorbent binder, wherein a "binder" is a material capable of attaching itself to a substrate, attaching other substances to a substrate, or attaching two substrates together. Flexible materials are desirable for use on animate or flexible objects.

Whereas most superabsorbent polymers require the addition of an internal crosslinker to reinforce the polymer, the polymer matrix material used in the present disclosure does not require the addition of a crosslinking agent because the organic monomers act as an internal crosslinker. The internal crosslinker allows the polymer matrix to be formed by coating the water-soluble precursor polymer onto the substrate and then removing the water to activate the latent crosslinker.

Soerens et al., in U.S. Pat. No. 6,737,491, describes an absorbent binder composition that may be used as a polymer matrix in the present disclosure. The absorbent binder composition disclosed in Soerens et al. is a monoethylenically unsaturated polymer and an acrylate or methacrylate ester that contains an alkoxysilane functionality that is particularly suitable for use in manufacturing absorbent articles. Also described in Soerens et al. is a method of making the absorbent binder composition that includes the steps of preparing a monomer solution, adding the monomer solution to an initiator system, and activating a polymerization initiator within the initiator system reported an alcohol-based, water-soluble binder composition. "Monomer(s)" as used herein includes monomers, oligomers, polymers, mixtures of monomers, oligomers and/or polymers, and any other reactive chemical species which are capable of co-polymerization with monoethylenically unsaturated carboxylic, sulphonic or phosphoric acid or salts thereof. Ethylenically unsaturated monomers containing a trialkoxysilane functional group are appropriate for this disclosure and are desired. Desired ethylenically unsaturated monomers include acrylates and methacrylates, such as acrylate or methacrylate esters that contain an alkoxysilane functionality.

The absorbent binder composition disclosed in the references noted above is the reaction product of at least 15 percent by mass monoethylenically unsaturated carboxylic, sulphonic or phosphoric acid or salts thereof, an acrylate or methacrylate ester that contains an alkoxysilane functionality which, upon exposure to water, forms a silanol functional group which condenses to form a crosslinked polymer, a copolymerizable hydrophilic glycol containing ester monomer; and/or, a plasticizer.

Desirably, the monoethylenically unsaturated monomer is acrylic acid. Other suitable monomers include carboxyl group-containing monomers: for example monoethylenically unsaturated mono or poly-carboxylic acids, such as (meth)acrylic acid (meaning acrylic acid or methacrylic acid; similar notations are used hereinafter), maleic acid, fumaric acid, crotonic acid, sorbic acid, itaconic acid, and cinnamic acid; carboxylic acid anhydride group-containing monomers: for example monoethylenically unsaturated polycarboxylic acid anhydrides (such as maleic anhydride); carboxylic acid salt-containing monomers: for example water-soluble salts (alkali metal salts, ammonium salts, amine salts, and the like) of monoethylenically unsaturated mono- or poly-carboxylic acids (such as sodium (meth) acrylate, trimethylamine (meth)acrylate, triethanolamine (meth)acrylate), sodium maleate, methylamine maleate; sulfonic acid group-containing monomers: for example aliphatic or aromatic vinyl sulfonic acids (such as vinylsulfonic acid, allyl sulfonic acid, vinyltoluenesulfonic acid, styrene sulfonic acid), (meth)acrylic sulfonic acids [such as sulfopropyl (meth)acrylate, 2-hydroxy-3-(meth)acryloxy propyl sulfonic acid]; sulfonic acid salt group-containing monomers: for example alkali metal salts, ammonium salts, amine salts of sulfonic acid group containing monomers as mentioned above; and/or amide group-containing monomers: vinylformamide, (meth)acrylamide, N-alkyl (meth)acrylamides (such as N-methylacrylamide, N-hexylacrylamide), N,N-dialkyl (meth)acryl amides (such as N,N-dimethylacrylamide, N,N-di-n-propylacrylamide), N-hydroxyalkyl (meth)acrylamides [such as N-methylol (meth)acrylamide, N-hydroxyethyl (meth)acrylamide], N,N-dihydroxyalkyl (meth)acrylamides [such as N,N-dihydroxyethyl (meth) acrylamide], vinyl lactams (such as N-vinylpyrrolidone).

Suitably, the amount of monoethylenically unsaturated carboxylic, sulphonic or phosphoric acid or salts thereof relative to the weight of the absorbent binder polymer composition may range from about 15 percent to about 99.9 percent by weight. The acid groups are desirably neutralized to the extent of at least about 25 mol percent, that is, the acid groups are preferably present as sodium, potassium or ammonium salts. The degree of neutralization is desirably at least about 50 mol percent.

Organic monomers capable of co-polymerization with monoethylenically unsaturated carboxylic, sulphonic or phosphoric acid or salts thereof, which monomers contain a trialkoxysilane functional group or a moiety that reacts with water to form a silanol group, are useful in the practice of this invention. The trialkoxysilane functional group has the following structure:

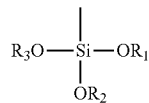

wherein R1, R2 and R3 are alkyl groups independently having from 1 to 6 carbon atoms.

Whereas most superabsorbent polymers require addition of an internal crosslinker to reinforce the polymer, the flexible superabsorbent binder polymer composition of the present disclosure does not require the addition of a crosslinking agent because the organic monomers including the trialkoxysilane functional act as an internal crosslinker. The internal crosslinker allows the superabsorbent binder polymer composition to be formed by coating the water-soluble precursor polymer onto the substrate and then removing the water to activate the latent crosslinker.

In addition to monomers capable of co-polymerization that contain a trialkoxysilane functional group, it is also feasible to use a monomer capable of co-polymerization that can subsequently be reacted with a compound containing a trialkoxysilane functional group or a moiety that reacts with water to form a silanol group can also be used. Such a monomer may contain, but is not limited to, an amine or an alcohol. An amine group incorporated into the co-polymer may subsequently be reacted with, for example, but not limited to, (3-chloropropyl) trimethoxysilane. An alcohol group incorporated into the co-polymer may subsequently be reacted with, for example, but not limited to tetramethoxysilane.

The amount of organic monomer having trialkoxysilane functional groups or silanol-forming functional groups relative to the weight of the polymeric binder composition may range from about 0.1% to about 15% by weight. Suitably, the amount of monomer should exceed 0.1% by weight in order provide sufficient crosslinking upon exposure to moisture. In some aspects, the monomer addition levels are between about 0.1% and about 20% by weight of the flexible superabsorbent binder polymer composition, such as, between about 0.5% and about 10% by weight of the flexible superabsorbent binder polymer composition; or between about 0.5% and about 5% by weight of the flexible superabsorbent binder polymer composition for some intended uses. The flexible superabsorbent binder polymer composition can include a copolymerizable hydrophilic glycol containing an ester monomer, for example a long chain, hydrophilic monoethylenically unsaturated esters, such as poly(ethylene glycol) methacrylate having from 1 to 13 ethylene glycol units. The hydrophilic monoethylenically unsaturated esters have the following structure:

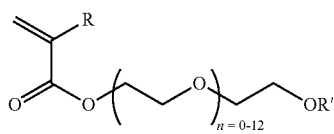

R=H or CH3
R'=H, alkyl, phenyl

The amount of monoethylenically unsaturated hydrophilic esters relative to the weight of the polymeric binder composition thereof may range from 0 to about 75% by weight of monomer to the weight of the flexible superabsorbent binder polymer composition. In some aspects, the monomer addition levels are between about 10% and about 60% by weight of the flexible superabsorbent binder polymer composition; such as between about 20% and about 50% by weight of the flexible superabsorbent binder polymer composition; or between about 30% and about 40% by weight of the flexible superabsorbent binder polymer composition for some intended uses.

In some aspects, the flexible superabsorbent binder polymer composition may also include a hydrophilic plasticizer. Suitable hydrophilic plasticizers that may be used include, but are not limited to a polyhydroxy organic compounds such as glycerin, and low molecular weight polyolefinic glycols such as polyethylene glycol (PEG) of molecular weight ranges from about 200 to about 10,000.

The amount of plasticizer relative to the weight of the flexible superabsorbent binder polymer composition thereof may range from 0 to about 75% by weight of plasticizer to the weight of the flexible superabsorbent binder polymer composition. In some aspects, the plasticizer addition levels are from about 10% to about 60% by weight of the flexible superabsorbent binder polymer composition; such as from about 10% to about 40% by weight of the flexible superabsorbent binder polymer composition for some intended uses.

In some aspects, the flexible superabsorbent binder polymer composition of the present invention may be made from monomers that include at least 15% by weight monoethylenically unsaturated monomer selected from carboxylic acid, carboxylic acid salts, sulphonic acid, sulphonic acid salts, phosphoric acid, or phosphoric acid salts; an initiator system; and an acrylate or methacrylate ester that contains a group readily transformed into a silanol functionality by subsequent reaction with water, wherein said the resulting flexible superabsorbent binder polymer composition has an average molecular weight of from about 100,000 to about 650,000 g/mole, such as about 100,000 to about 300,000 g/mole, and the superabsorbent polymer composition has a viscosity of less than about 10,000 cps and a residual monoethylenically unsaturated monomer content of less than about 1000 ppm.

One of the issues in preparing water-soluble polymers is the amount of the residual monoethylenically unsaturated monomer content remaining in the polymer. For applications in personal hygiene it is required the amount of residual monoethylenically unsaturated monomer content of the superabsorbent polymer composition be less than about 1000 ppm, and more preferably less than 500 ppm, and even more preferably less than 100 ppm. U.S. Pat. No. 7,312,286 discloses at least one method by which an absorbent binder composition may be manufactured so that the residual monoethylenically unsaturated monomer content is at least less than 1000 parts per million. The analysis of residual monoethylenically unsaturated monomer is determined according to the Residual Monoethylenically Unsaturated Monomer Test.

Several types of viruses may be added to the polymer matrix, e.g. bacteriophage, mycophage, and protozoan, and arthropod viruses. Regardless of the type of virus used, the desired quantity of virus in the polymer matrix is the same. In one aspect, the desired quantity is at least 0.5 virus per mg of polymer. In another aspect, the quantity ranges from about 1 virus per mg of polymer to about $10^4$ virus per mg of polymer. In another aspect, the desired quantity ranges from about 50 virus per mg of polymer to about 1000 virus per mg of polymer. The most desirable quantity is about 100 virus per mg of polymer.

In another embodiment of the present disclosure, the polymer matrix is one of the polymer solutions listed in U.S. Patent Publication 2012/0171155, filed Dec. 30, 2010, and incorporated herein by reference. Such polymers include cationic amine polymer-epichlorohydrin adduct, cationic amine polymer-epichlorohydrin resin, poly(methacrylamidopropyltrimethylammonium) chloride, poly(bis(2-chloroethyl)ether-alt-1,3-bis(dimethylamino)propyl)urea, poly(diallyldimethylammonium) chloride, poly(t-butyl acrylate co-ethyl acrylate co-methacrylic acid), polyethylene oxide, polyquaternium-16, polyquaternium-22, polyquaternium-67 and mixtures of such polymers.

Bacteriophage

A bacteriophage is a virus that infects and replicates within bacteria. Bacteriophages have been used for over 90 years as an alternative to antibiotics. They are a possible therapy against multi-drug-resistant strains of many bacteria.

Bacteriophages are composed of proteins that encapsulate a DNA or RNA genome, and may have relatively simple or elaborate structures. Their genomes may encode as few as four genes, and as many as hundreds of genes. Bacteriophage replicate within bacteria following the injection of their genome into the cytoplasm.

Bacteriophages are widely distributed in locations populated by bacterial hosts, such as soil or the intestines of animals. One of the densest natural sources for phages and other viruses is sea water.

Suitable bacteriophages include M13, T phage, lambda phage, MS2, G4, Phix174, and Phi6, K. Such materials are available from American Type Culture Collection ("ATCC"), Manassas, Va., or directly isolated from nature as is known in the art.

Mycophage

A mycophage is a virus that infects and replicates within fungi.

Suitable mycophages include $PS_I$. Such material is available from American Type Culture Collection ("ATCC"), Manassas, Va.

Protozoan Viruses

In the context of the present disclosure, protozoan viruses are viruses that kill protozoa such as amoeba, *plasmodium*, etc. Suitable protozoan viruses include dsRNA viruses for *Trichomonas vaginalis* (Trichomonasvirus), *Giardia lamblia* (Giardiavirus), Cryptosproridium (Cryptovirus), *Leish-* mania braziliensis, the *Babesia* spp., the *Eimeria* spp. Suitable amoeba viruses include *Acanthamoeba polyphaga* marseillevirus (APMaV), *Acanthamoeba castellanii* lausannevirus (ACLaV), *Acanthamoeba polyphaga* mimivirus (APMV).

Such materials are obtained from natural sources as is known in the art.

Arthropod Viruses

Arthropods are a class of invertebrates that includes crustaceans. In the context of the present disclosure, arthropod viruses are viruses that kill viruses transmitted by arthropod vectors ("arboviruses"). Suitable arthropod viruses include baculoviruses. Such materials are obtained from natural sources as is known in the art.

Method of Use

The compositions of the present disclosure may be applied to a targeted surface directly, in liquid form, such as by a spray bottle or similar packaging capable of delivering a liquid composition in a relatively uniform amount over the full surface to be covered. Further, articles to be protected by the compositions of the present disclosure may be dipped therein. In addition, because the compositions are liquid at room temperature, the composition may be applied to a surface by wiping the surface with an article that has been saturated with the composition; the composition will transfer from the article to the surface. Such articles include brushes, rollers, and wipes or wipers formed from a basesheet. It is further contemplated that the composition of the present disclosure be applied to a surface as a wettable powder.

A wiper or wipe basesheet may be formed from one or more woven materials, nonwoven materials, cellulosic materials and combinations of such materials. More specifically, the basesheet may be formed of nonwoven fibrous sheet materials that include meltblown, spunlace, coform, air-laid, bonded-carded web materials, hydroentangled materials and combinations of such materials. Such materials can be made of synthetic or natural fibers or a combination of such fibers. Typically, the basesheet will have a basis weight of from 25 grams per square meter to 120 grams per square meter and desirably from 40 grams per square meter to 90 grams per square meter.

In the alternative, the wiper or wipe basesheet may be constructed of a coform material of polymer fibers and absorbent fibers having a basis weight of from 45 to 80 grams per square meter and desirably 60 grams per square meter. Typically, such coform basesheets are constructed of a gas-formed matrix of thermoplastic polymeric meltblown fibers and cellulosic fibers. Various suitable materials may be used to provide the polymeric meltblown fibers, such as, for example, polypropylene microfibers. Alternatively, the polymeric meltblown fibers may be elastomeric polymer fibers, such as those provided by a polymer resin. For instance, VISTAMAXX elastic olefin copolymer resin designated PLTD-1810, available from ExxonMobil Corporation of Houston, Tex., or KRATON G-2755, available from Kraton Polymers of Houston, Tex., may be used to provide stretchable polymeric meltblown fibers for the coform basesheets. Other suitable polymeric materials or combinations thereof may alternatively be utilized as known in the art.

The coform basesheet additionally may be constructed of various absorbent cellulosic fibers, such as, for example, wood pulp fibers. Suitable commercially available cellulosic fibers for use in the coform basesheets can include, for example, NF 405, which is a chemically treated bleached southern softwood Kraft pulp, available from Weyerhaeuser Co. of Washington, D.C.; NB 416, which is a bleached southern softwood Kraft pulp, available from Weyerhaeuser Co.; CR-0056, which is a fully debonded softwood pulp, available from Bowater, Inc. of Greenville, S.C.; Golden Isles 4822 debonded softwood pulp, available from Koch Cellulose of Brunswick, Ga.; and SULPHATATE HJ, which is a chemically modified hardwood pulp, available from Rayonier, Inc. of Jessup, Ga. The relative percentages of the polymeric meltblown fibers and cellulosic fibers in the conform base sheet may vary over a wide range depending upon the desired characteristics of the wipes. For example, the conform base sheet may have from 10 weight percent to 90 weight percent, desirably from 20 weight percent to 60 weight percent, and more desirably from 25 weight percent to 35 weight percent of polymeric meltblown fibers based on the dry weight of the conform base sheet.

The compositions of the invention may be incorporated into the basesheet in an add-on amount of from 50% (by weight of the basesheet) to 800% (by weight of the basesheet). More specifically, the compositions may be incorporated into the basesheet in an add-on amount of from 200% (by weight of the basesheet) to 600% (by weight of the basesheet) or from 400% (by weight of the basesheet) to 600% (by weight of the basesheet). The composition add-on amounts may vary depending on the composition of the basesheet.

EXAMPLES

A bacteriophage was mixed into a polymer matrix consisting of a flexible superabsorbent polymer manufactured by Evonik Stockhausen, LLC (Greensboro, N.C., U.S.A.) in accordance with U.S. Pat. No. 7,312,286 (hereinafter referred to as "FAB"). The mixture was left to dry on a specimen surface at room temperature and ambient relative humidity. Once the mixture was dry to the touch, *E. coli* ATCC 13706 was applied to the surface. The specimen was held in the test environment for 18 hours after which the surface was extracted and the number of bacteriophage counted. A positive result is defined as one that shows that the *E. coli* challenged surface has more bacteriophage than a surface not challenged by *E. coli.*

Materials

TABLE 1

POLYMER

| Ingredient | Weight % Composition | CAS Number |
|---|---|---|
| Polyacrylic acid, sodium salt | 20-40 | 9003-04-7 |
| Polyethylene glycol (PEG400) | <5 | 25322-68-3 |
| Water | Remainder | 7732-18-5 |
| Potential Residuals | ppm in FAB | CAS Number |
| Acrylic acid | 1000 | 79-10-7 |
| 3-trimethoxysilyl propyl methacrylate (MEMO) | 50 | 2530-85-0 |

Test Protocol

1. Aliquot 10.8 ml of the polymer of Table 1 ("FAB") into a 15-mL conical centrifuge tube.

2. Add 1.2 mL of PhiX-174 bacteriophage (ATCC 13706-61) at $10^8$ PFU/mL into the FAB. Mix by inverting tube.

3. Aliquot 2.0 mL of PhiX-174/FAB to 4 wells of a 6-well microplate.

4. Allow the FAB to dry at room temperature, ambient humidity for 2 hours.

5. Add 200 μL of *Escherichia coli* ATCC 13706 to 2 wells containing PhiX-174/FAB. Mix with pipette tip.

6. Add 200 ul of buffer to 2 wells containing the PhiX-174/FAB. Mix with pipette tip.

7. Allow plate to dry for 18 hours, preferably under a laminar flow hood.

8. Prepare a bacteriophage suspension by adding 200 μL of 108 PFU/mL PhiX-174 to 10 mL of deionized water.

9. Re-suspend the dried PhiX-174/FAB and bacteriophage suspension in 30.0 mL of sterile deionized water.

10. Vortex the suspension with sterile beads for 30 seconds and invert tubes to finish mixing.

11. Dilute and plate the suspension using a positive displacement pipette as follows:
   a. Add 100 μl of *E. coli* ATCC 13706 to 4 ml of molten soft agar and vortex.
   b. Aliquot 100 μl of PhiX-174 dilutions to 4 ml of molten *E-coli* soft agar and vortex.
   c. Pour molten top agar on TSA plate and cover surface of plate with top agar.
   d. Incubate at 37° C. for 24 hours and count PFU.

Results

TABLE 2

| Test Code | Average LOG PFU/mL | LOG PFU/mL increase |
| --- | --- | --- |
| PhiX-174 bacteriophage + FAB | 2.0 | 0 |
| PhiX-174 bacteriophage + *E. coli* ATCC 13706 | 4.7 | 2.7 |

As seen in Table 2, a 2.7 LOG PFU/mL increase in the number of bacteriophage was observed. This indicates when the polymer is contaminated with bacteria, the polymer is providing an environment that not only allows the bacteriophage to infect contaminating bacteria, but also to replicate inside the bacteria. Once the bacteria lyses, the progeny bacteriophage are released, replenishing the quantity of bacteriophage within the polymer. Providing this environment of bacteriophage replication allows the bacteriophage concentration within the polymer to be continuously maintained as bacterial contamination events occur. With the polymer absent, the bacteriophage are not able to replicate within the bacteria.

TABLE 3

| Test Code | Average LOG PFU/mL | LOG PFU/mL increase |
| --- | --- | --- |
| PhiX-174 bacteriophage + Polyurethane diol | 5.1 | 0 |
| PhiX-174 bacteriophage + *E. coli* ATCC 13706 | 5.2 | 0.1 |

As seen in Table 3, the inclusion of polyurethane diol did not support the production of progeny bacteriophage and therefore is not preferred for this application. Compared to a mixture containing only PhiX-174+*E. coli*, the combination of PhiX-174+*E. coli*+polyurethane diol did not increase the concentration of PhiX-174 bacteriophage.

TABLE 4

| Test Code | Average LOG PFU/mL | LOG PFU/mL increase |
| --- | --- | --- |
| PhiX-174 bacteriophage + 0.7% w/w Agar | 4.3 | 0 |
| PhiX-174 bacteriophage + *E. coli* ATCC 13706 | 6.7 | 2.4 |

As seen in Table 4, the inclusion of 0.7% w/w agar supported the production of progeny bacteriophage. Compared to a mixture containing only PhiX-174+*E. coli*, the combination of PhiX-174+*E. coli*+0.7% w/w agar increased the concentration of PhiX-174 bacteriophage by 2.4 LOG PFU/mL.

TABLE 5

| Test Code | Average LOG PFU/mL | LOG PFU/mL increase |
| --- | --- | --- |
| PhiX-174 bacteriophage + Hydroxypropyl Cellulose | 4.2 | 0 |
| PhiX-174 bacteriophage + *E. coli* ATCC 13706 | 4.3 | 0.1 |

As seen in Table 5, the inclusion of hydroxypropyl cellulose did not support the production of progeny bacteriophage and therefore is not preferred for this application. Compared to a mixture containing only PhiX-174+*E. coli*, the combination of PhiX-174+*E. coli*+hydroxypropyl cellulose did not increase the concentration of PhiX-174 bacteriophage.

TABLE 6

| Polymer | LOG PFU/mL increase* |
| --- | --- |
| Polyurethane diol | 0.1 |
| Agar (0.7% w/w) | 2.4 |
| Hydroxypropyl Cellulose | 0.1 |

**0 PFU recovered when cellolose was present

As seen in Table 6, a LOG 10 PFU/mL increase of PhiX-174 concentration occurred when co-incubated with *E. coli* was observed with 0.7% w/w agar present, similar to the results observed with the inclusion of the FAB polymer. The inclusion of polyurethane diol or hydroxypropyl cellulose did not provide an increase in PhiX-174 concentration.

Test Methods

Residual Monoethylenically Unsaturated Monomer Test Method

The residual monoethylenically unsaturated monomer analysis is carried out using solid film obtained from the polymer solution or superabsorbent composition. By way of example for this test description, the monoethylenically unsaturated monomer is acrylic acid. High performance liquid chromatography (HPLC) with a SPD-10Avp Shimadzu UV detector (available from Shimadzu Scientific Instruments, having a place of business in Columbia, Md., U.S.A) is used to determine the residual acrylic acid monomer content. To determine the residual acrylic acid monomer, about 0.5 grams of cured film is stirred in 100 ml of a 0.9% NaCl-solution for 16 h using a 3.5 cm L.times.0.5 cm W magnetic stirrer bar at 500 rpm speed. The mixture is filtered and the filtrate is then passed through a Nucleosil C8 100 A reverse phase column (available from Column Engineering Incorporated, a business having offices located in Ontario, Calif., U.S.A.) to separate the acrylic acid monomer. The acrylic acid monomer elutes at a certain time with detection limit at about 10 ppm. The peak area of resulting elutes calculated from the chromatogram is then used to calculate the amount of residual acrylic acid monomer in the film. Initially, a calibration curve was generated by plotting the response area of pure acrylic acid elutes against its known amount (ppm). A linear curve with a correlation coefficient of greater than 0.996 was obtained.

Water of Activity Test Method

Water activity ($a_w$), not water content, determines the lower limit of available water for microbial growth. While temperature, pH, and several other factors can influence whether an organism will grow the rate at which it will grow, water activity is often the most important factor for growth. The lowest aw at which the vast majority of bacteria will grow is about 0.90. The $a_w$ for molds and yeast growth is about 0.61.

Water activity instruments measure the energy status (sometimes referred to as free, unbound or active water) of the water present in a sample. A portion of the total water content present in sample is strongly bound to specific sites on the components in the sample. These sites may include the hydroxyl groups of polysaccharides, the carbonyl and amino groups of proteins, and other polar sites. Water is held by hydrogen, iondipole, and other strong chemical bonds.

A number of instruments are available to measure aw. Water activity values are obtained by either a resistive electrolytic, a capacitance or a dew point hygrometer measurements. A specific example of a method that can be used to measure the Aw is the use of Rotronic AG Water Activity and Temperature Probe HC2-AW-USB (Bassersdorf, Switzerland) (the "probe"). To use this system the following procedure is followed:

1. Measure water activity only in a temperature stable area.
2. For best accuracy, temperature should not change by more than 0.01° C./minute.
3. Prior to measurements, place each product sample in a covered disposable sample cup.
4. Place the cups in the same general area as the probe.
5. Prior to using the probe, verify the integrity and cleanliness of the sealing O-ring located under the probe.
6. Allow for sufficient time for the samples to come to the temperature of the probe (25° C.).
7. Set the dwell time to an appropriate time interval. Measurements typically require about 5 minutes.
8. When temperature conditions are stable (both at the product and probe), use the probe to take measurements and record.

While the present invention has been described in detail with reference to the preferred embodiments, those skilled in the art will appreciate that various modifications and substitutions can be made thereto without departing from the spirit and scope of the present invention as set forth in the appended claims.

The invention claimed is:

1. A composition for protecting a surface from pathogenic organisms, the composition comprising:
   a hydrophilic polymer matrix; and
   a pathogen-associated virus that replicates upon exposure to pathogenic organisms, the pathogen-associated virus being disposed within the polymer matrix;
   wherein the polymer matrix allows the virus to replicate to support antimicrobial activity after the composition dries and upon being exposed to pathogenic organisms, and wherein the polymer matrix is a flexible absorbent binder comprising a monoethylenically unsaturated polymer and an acrylate or methacrylate ester including an alkoxysilane functionality.

2. The composition of claim 1 wherein the pathogenic organisms are fungal.

3. The composition of claim 1 wherein the pathogenic organisms are bacterial.

4. The composition of claim 1 wherein the polymer matrix can maintain a Water of Activity of greater than 0.65 for 5 to 40 minutes of exposure to pathogenic organisms as measured by use of a Rototronic AG Water Activity and Temperature Probe.

5. The composition of claim 1 wherein the virus is a bacteriophage.

6. The composition of claim 1 wherein the virus is a mycophage.

7. The composition of claim 1 wherein the virus is selected from the group consisting of an arthropod virus, an amoeba virus, and a protozoan virus.

8. An antimicrobial wipe or wiper comprising:
   an antimicrobial composition comprising a hydrophilic polymer matrix; and
   a pathogen-associated virus that replicates upon exposure to pathogenic organisms, the pathogen-associated virus being disposed within the polymer matrix; wherein the polymer matrix allows the virus to replicate to support antimicrobial activity after the composition dries, and wherein the polymer matrix is selected from the group consisting of: flexible absorbent binder comprising a monoethylenically unsaturated polymer and an acrylate or methacrylate ester including an alkoxysilane functionality, cationic amine polymer-epichlorohydrin adduct, cationic amine polymer-epichlorohydrin resin, poly-(methacrylamidopropyltrimethylammonium) chloride, poly(bis(2-chloroethylether-alt-1,3-bis(dimethylamino)propyl)urea, poly(diallyldimethylammonium) chloride, poly(t-butyl acrylate co-ethyl acrylate co-methacrylic acid); polyethylene oxide, polyquaternium-16, polyquaternium-22; and mixtures thereof; and a basesheet; wherein the basesheet is saturated with the antimicrobial composition.

9. The antimicrobial wipe or wiper of claim 8, wherein the base sheet comprises thermoplastic fibers and cellulose fibers.

10. The antimicrobial wipe or wiper of claim 8 wherein the basesheet comprises a non-woven material.

11. The antimicrobial wipe or wiper of claim 8 wherein the virus comprises a bacteriophage and/or a mycophage.

12. A composition for protecting a surface from pathogenic organisms, the composition comprising:
   a hydrophilic polymer matrix; and a pathogen-associated virus that replicates upon exposure to pathogenic organisms, the pathogen-associated virus being disposed within the polymer matrix; wherein the polymer matrix allows the virus to replicate to support antimicrobial activity after the composition dries and upon being exposed to pathogenic organisms, and wherein the polymer matrix is selected from the group consisting of cationic amine polymer-epichlorohydrin adduct, cationic amine polymer-epichlorohydrin resin, poly-(methacrylamidopropyltrimethylammonium) chloride, poly(bis(2-chloroethyl)ether-alt-1,3-bis(dimethylamino)propyl)urea, poly(diallyldimethylammonium) chloride, poly(t-butyl acrylate co-ethyl acrylate co-methacrylic acid), polyethylene oxide, polyquaternium-16, polyquaternium-22, and mixtures thereof.

13. The composition of claim 12, wherein the polymer matrix is configured to maintain a Water of Activity of greater than 0.65 for 5 to 40 minutes of exposure to pathogenic organisms as measured by use of a Rototronic AG Water Activity and Temperature Probe.

* * * * *